United States Patent [19]

Doan

[11] Patent Number: 4,731,058
[45] Date of Patent: Mar. 15, 1988

[54] DRUG DELIVERY SYSTEM

[75] Inventor: Phong D. Doan, Shoreview, Minn.

[73] Assignee: Pharmacia Deltec, Inc., St. Paul, Minn.

[21] Appl. No.: 865,687

[22] Filed: May 22, 1986

[51] Int. Cl.$^4$ ............................................. A61M 5/20
[52] U.S. Cl. .............................. 604/155; 128/DIG. 1; 222/63; 222/333; 604/245
[58] Field of Search ................ 128/DIG. 1, DIG. 12; 604/153, 154, 155, 131, 191, 245, 246; 222/23, 55, 63, 333

[56] References Cited

U.S. PATENT DOCUMENTS

| | | | |
|---|---|---|---|
| 2,602,446 | 7/1952 | Glass et al. | |
| 3,415,419 | 12/1968 | Jewett et al. | 222/333 |
| 3,425,416 | 2/1969 | Loughry. | |
| 3,701,350 | 10/1972 | Guenther | 604/155 |
| 3,720,211 | 3/1973 | Kyrias. | |
| 3,812,843 | 5/1974 | Wootten et al. | 604/155 |
| 3,858,581 | 1/1975 | Kamen. | |
| 4,067,332 | 1/1978 | O'Leary. | |
| 4,080,967 | 3/1978 | O'Leary. | |
| 4,255,096 | 3/1981 | Coker, Jr. et al. | |
| 4,367,435 | 1/1983 | Bailey et al. | |
| 4,424,720 | 1/1984 | Bucchianeri. | |
| 4,435,173 | 3/1984 | Siposs et al. | |
| 4,465,474 | 8/1984 | Mardorf et al. | 128/DIG. 1 |
| 4,465,475 | 8/1984 | Mardorf et al. | |
| 4,544,369 | 10/1985 | Skakoon et al. | 128/DIG. 12 |
| 4,563,175 | 1/1986 | LaFond. | |
| 4,627,835 | 12/1986 | Fenton, Jr. | 128/DIG. 1 |
| 4,635,820 | 1/1987 | Marshall | 222/63 |

OTHER PUBLICATIONS

Prominject ® Service Manual, pp. 1–4, by Pharmacia AB, S-751 82, Uppsala, Sweden.
Auto Syringe ® Model AS5C, Infusion Pump Operator's Manual, pp. 8–15, Copyrighted 1984, by Travenol Laboratories, Inc., Auto Syringe Div., Hookset, N.H., 03104.

*Primary Examiner*—Stephen C. Pellegrino
*Assistant Examiner*—Ralph Lewis
*Attorney, Agent, or Firm*—Peterson, Wicks, Nemer & Kamrath

[57] ABSTRACT

A system for delivering a drug to a patient according to the preferred embodiment of the present invention is shown as including a plunger assembly reciprocally received in a reservoir for forcing the drug therefrom for delivery to the patient. The plunger assembly is axially advanced by the rotation of a lead screw rotatably mounted and axially movable with respect to the chassis. In a first axial position, the end of the lead screw deflects contacts of a switch member into electrical engagement which interrupts operation of the motor which rotates the lead screw. The lead screw is biased out of its first axial position such that the first end of the lead screw does not actuate the switch member and rotation of the lead screw is not interrupted. An increase in the force necessary to advance the plunger assembly into the reservoir due to excessive reservoir back pressure caused by occlusion, plunger assembly friction, a depleted reservoir, and like conditions will cause the lead screw to move into its first axial position against its bias and to actuate the switch member.

31 Claims, 3 Drawing Figures

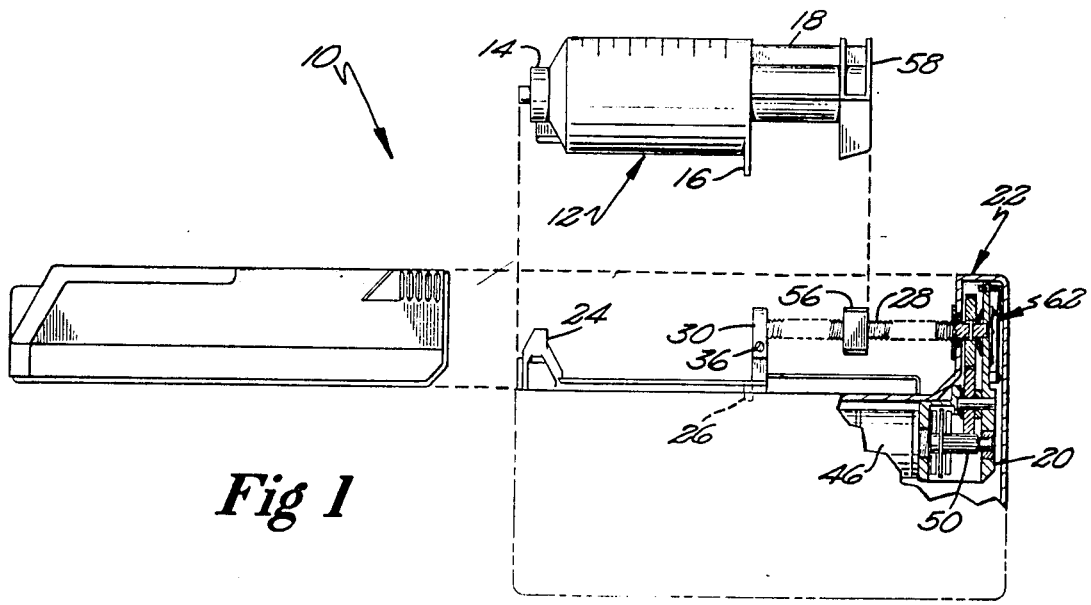
*Fig 1*
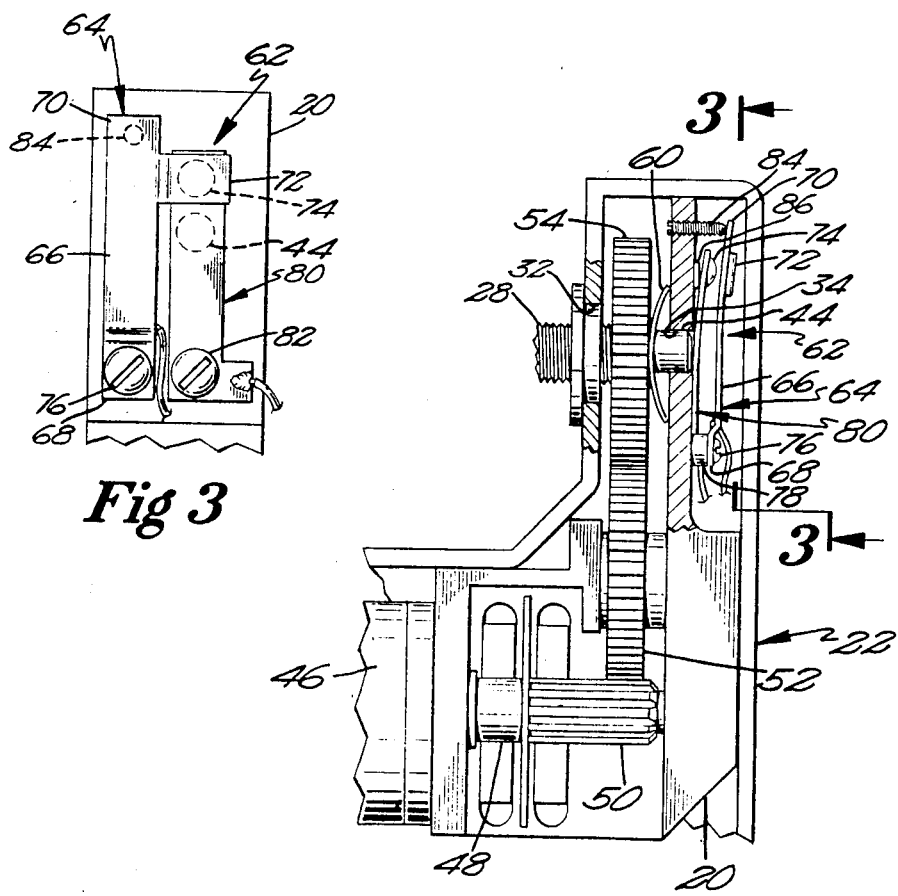
*Fig 3*
*Fig 2*

DRUG DELIVERY SYSTEM

BACKGROUND

The present invention relates generally to the delivery of drugs to patients, particularly to systems for providing drug delivery, and specifically, to systems for providing continuous drug delivery.

Certain drugs rarely achieve their maximum therapeutic action through conventional injection techniques. The therapeutic activity of such a drug is improved considerably when it is delivered at controlled rates to maintain optimum drug concentration for a specific period. In a typical drug injection, a greater dosage than necessary must be administered to keep the drug concentration within the effective therapeutic margin for the minimum period needed for treatment. With controlled drug infusion, the drug can be given at a precise rate that will keep the drug serum concentration within the therapeutic margin and out of the toxic range. Continuous drug delivery is assuming an ever increasing role in the treatment of acute and chronic illnesses. Many drugs reach their full potential only through precise delivery over an extended period of time.

Continuous intravenous infusion has been the only conventional method of administering drugs at constant controllable rates for prolonged periods. Conventional equipment requires the patient to be hospitalized and attended by medical professionals frequently. These requirements make the system somewhat impractical and expensive for a non-critical patient who could be treated outside the hospital.

One system for providing continuous drug delivery to a patient at a controllable rate which does not require frequent medical attention and which allows the patient to be ambulatory is a syringe pump. However, a need has arisen in drug delivery systems and especially in syringe pumps for mechanisms for interrupting the normal advancement of the plunger assembly in the reservoir and sounding an audible alarm under certain actuation conditions, such as occluded catheter and empty reservoir. It is further necessary to limit the pressure generated by the drug delivery system in the event of an occlusion. It is advantageous to interrupt the normal operation of the system and sound an alarm as promptly as possible following an occlusion or empty reservoir condition. It is also advantageous to be able to adjust the threshold of pressure necessary to actuate the interruption of operation and alarm.

SUMMARY

The present invention solves these and other needs by providing, in the preferred embodiment, a system for delivering a drug to a patient by advancing a plunger assembly in a reservoir. The drug delivery system includes a lead screw mounted for rotation and at least limited axial movement from a first axial position with respect to a chassis. The plunger assembly is advanced in the reservoir in response to rotation of the lead screw. The lead screw is axially biased with respect to the chassis in the advancement direction of the plunger assembly into the reservoir and out of its first axial position. The drug delivery system according to the teachings of the present invention further includes a member actuated by the first end of the lead screw for interrupting the rotation of the lead screw when the lead screw is moved into its first axial position against its bias as the result of an increase of force necessary to advance the plunger assembly into the reservoir due to excessive reservoir back pressure caused by occlusion, plunger assembly friction, a depleted reservoir, and like conditions.

It is thus an object of the present invention to provide a novel drug delivery system.

It is further an object of the present invention to provide such a novel drug delivery system including provisions for interrupting rotation of the lead screw in the event of an increase of force necessary to advance the plunger assembly into the reservoir due to excessive reservoir back pressure caused by occlusion, plunger assembly friction, a depleted reservoir, and like conditions.

It is further an object of the present invention to provide such a novel drug delivery system having a simplified construction utilizing a biased lead screw to itself actuate the lead screw rotation interrupting provisions.

It is further an object of the present invention to provide such a novel drug delivery system which is more sensitive to interrupting actuation conditions.

It is further an object of the present invention to provide such a novel drug delivery system which is faster to interrupt normal drug delivery.

It is further an object of the present invention to provide such a novel drug delivery system which allows more precise calibration.

It is further an object of the present invention to provide such a novel drug delivery system having reduced drug shortfall during pressure buildup.

It is further an object of the present invention to provide such a novel drug delivery system having a minimum amount of components greatly increasing the ease of assembly.

It is further an object of the present invention to provide such a novel drug delivery system permitting an effective water-resistant seal.

It is further an object of the present invention to provide such a novel drug delivery system having provisions for adjustment of actuation conditions.

It is further an object of the present invention to provide such a novel drug delivery system allowing preset thrust threshold actuation.

These and further objects and advantages of the present invention will become clearer in light of the following detailed description of an illustrative embodiment of this invention described in connection with the drawings.

DESCRIPTION OF THE DRAWINGS

The illustrative embodiment may best be described by reference to the accompanying drawings where:

FIG. 1 shows a side elevational view of a drug delivery system according to the preferred teachings of the present invention, with portions thereof being exploded and broken away.

FIG. 2 shows a partial, cross-sectional view of the drug delivery system of FIG. 1.

FIG. 3 shows a partial, cross-sectional view of the drug delivery system of FIG. 1 according to section line 3—3 of FIG. 2.

All figures are drawn for ease of explanation of the basic teachings of the present invention only; the extensions of the Figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "top", "bottom", "upper", "lower", "first", "second", "inside", "outside", and similar terms are used herein, it should be understood that these terms have reference only to the structure shown in the drawings as it would appear to a person viewing the drawings and are utilized only to facilitate describing the invention.

DESCRIPTION

A drug delivery system according to the preferred form of the present invention is shown in the drawings as a syringe pump and generally designated 10. Drug delivery system 10 in its most preferred form includes a reservoir 12 shown as a syringe barrel for storing the drug to be delivered to the patient by system 10. Reservoir 12 includes a first, frustoconical-shaped discharge end 14 and a second, open end including a radially extending mounting tab 16. Drug delivery system 10 in its most preferred form includes a plunger assembly 18 reciprocally received in reservoir 12 for forcing the drug located therein through end 14 and a suitable medication catheter or tube, not specifically shown, to the patient when plunger assembly 18 is advanced into reservoir 12.

In its most preferred form, drug delivery system 10 includes a chassis 20 removably captured in a housing 22. Reservoir 12 is fixed to housing 22 and thus to chassis 20 by upstanding cradle member 24 having a size and shape complementary to and for receiving frustoconical-shaped discharge end 14 of reservoir 12 and by a mounting recess 26 for removable receipt of mounting tab 16. Housing 22 may include a reservoir cover which is shown in its most preferred form as being slidably mounted to housing 22.

A lead screw 28 is further provided according to the teachings of the present invention. Specifically, lead screw 28 is mounted for rotation and at least limited axial movement from a first axial position with respect to chassis 20 and housing 22 by mounting jaws 30 secured to housing 22 adjacent to mounting recess 26 and by mounting bores 32 and 34 formed in housing 22 and chassis 20, respectively. In its most preferred form, jaws 30 include a first jaw integrally formed with housing 22 and a second jaw removably secured to the first jaw by a bolt 36. In its most preferred form, first and second jaws 30 each include a semicircular-shaped trough for receipt of lead screw 28. One of the first and second jaws 30 includes a projection for receipt in a complementary depression formed in the other jaw 30 on the side of the troughs opposite housing 22 and with bolt 36 located on the side of the troughs adjacent housing 22. The first end 44 of lead screw 28 extends through chassis 20.

In its most preferred form for rotating lead screw 28 with respect to chassis 20 and housing 22, motor 46 having an output shaft 48 is provided. Suitable gearing may then be provided for rotatably relating output shaft 48 with lead screw 28 such as pinion gear 50 formed on output shaft 48 in gearing relation with idler gear 52 rotatably mounted in chassis 20 in gearing relation with lead screw gear 54 rotatably fixed to lead screw 28. Thus, when output shaft 48 is rotated by motor 46, lead screw 28 is rotated by gears 50, 52 and 54. It should then be noted that due to the provision of axially extending teeth of gears 52 and 54, limited axial movement is provided between gears 52 and 54. A drive nut 56 is threadably received on lead screw 28 and is removably attached in a nonrotatable manner to the free end 58 of plunger assembly 18 for axially reciprocating plunger assembly 18 with respect to reservoir 12 in response to the rotation of lead screw 28 by motor 46 and gears 50, 52 and 54.

In its most preferred form to allow assembling gear 54 on lead screw 28 and intermediate housing 22 and chassis 20, gear 54 is slidably but rotatably related to lead screw 28 such as by a pin extending radially from lead screw 28 into a complementary slot formed in gear 54 and drug delivery system 10 includes a member 60 for axially biasing gear 54 with respect to lead screw 28 in the direction of axial movement of plunger assembly 18 for advancing plunger assembly 18 into reservoir 12 for forcing the drug from reservoir 12. In its most preferred form, axially biasing member 60 is shown as a wave-spring washer of a very light compressive force located on lead screw 28 between lead screw gear 54 and chassis 20.

In its most preferred form, drug delivery system 10 includes a switch member 62 actuated by first end 44 of lead screw 28 for interrupting the operation of motor 46 and gears 50, 52 and 54 by electrically interrupting the control of motor 46 when lead screw 28 is moved against a bias into its first axial position. In its most preferred form, switch member 62 includes a first contact 64 mounted in a spaced relation from chassis 20. In its most preferred form, contact 64 is generally T-shaped having an elongated first leg 66 including a first end 68 and a second end 70 and a second leg 72. Leg 72 extends generally perpendicularly from leg 66 adjacent to its second end 70. Contact 64 is secured to chassis 20 by bolt 76 extending through leg 66 of contact 64 adjacent first end 68 and threadably received into chassis 20 with an insulating washer 78 sandwiched therebetween. To further space leg 72 of contact 64 from chassis 20, leg 66 includes a stepped portion on the side of bolt 76 opposite first end 68 and leg 72 includes a stepped portion adjacent to its interconnection to leg 66. Leg 72 of contact 64 is located on the side of lead screw 28 and its first end 44 opposite to end 68 and bolt 76.

In its most preferred form, switch member 62 further includes a second, spring contact 80 having its first end secured to chassis 20 by bolt 82 extending through contact 80 and threadably received into chassis 20 and having an engagement detent 74 located adjacent its second end and in generally axial alignment with and intermediate leg 72 of contact 64 and chassis 20. Detent 74 is provided in the preferred form to provide a repeatable point engagement with contact 64. It should then be noted that contact 80 is positioned such that detent 74 of contact 80 is normally spaced from leg 72 of contact 64. First end 44 of lead screw 28 is in axial alignment with and abuts with contact 80 intermediate engagement detent 74 and bolt 82. It should then be noted that spring contact 80 is movable to electrically engage contact 64 when lead screw 28 is in its first axial position.

It can then be appreciated that in the preferred form, contact 80 is formed as a spring contact for axially biasing lead screw 28 with respect to chassis 20 out of its first axial position and in the direction of axial movement of plunger assembly 18 for advancing plunger assembly 18 into reservoir 12 for forcing the drug from reservoir 12. Specifically, in the preferred form, contact 80 is formed of annealed copper beryllium heat treated to a spring temper and is plated with nickel and gold to insure electrical conductivity.

In its most preferred form, drug delivery system 10 according to the teachings of the present invention includes a member 84 for adjusting the spacing of leg 72 of contact 64 from chassis 20 and thus the spacing between leg 72 of contact 64 from detent 74 of contact 80. In its most preferred form, member 84 is shown as a set screw threadably received in chassis 20 and abutting with leg 66 of contact 64 adjacent its second end 70. Thus, by turning set screw 84 in or out of chassis 20, set screw 84 will hold contact 64 at adjustable spacing from chassis 20 and contact 80. As the force required to overcome the bias of spring contact 80 is directly related to the axial displacement of lead screw 28 required before switch member 62 interrupts the operation of motor 46, the thrust threshold required to actuate switch member 62 may be varied according to the position of set screw 84 adjusting the spacing of contact 64.

Additionally, in its most preferred form, spring contact 80 of drug delivery system 10 according to the teachings of the present invention is preloaded to thus reduce the axial displacement of lead screw 28 required before actuation while maintaining the desired thrust threshold force. Specifically, in the preferred embodiment, a spacer 86 is provided between the free end of spring contact 80 and chassis 20 to preload spring contact 80. It can then be appreciated that preloading spring contact 80 allows utilization of a spring contact 80 having a lesser spring tension.

Now that the construction of drug delivery system 10 according to the preferred form of the present invention has been set forth, the operation and subtle features of the present invention can be set forth and appreciated. Assuming that drug delivery system 10 includes at least a partially filled reservoir 12 and free end 58 of plunger assembly 18 is positioned on drive nut 56, the operator of drug delivery system 10 can program the microprocessor thereof to control the operation of motor 46 which in turn rotates lead screw 28 through gears 50, 52, and 54 which in turn advances plunger assembly 18 through drive nut 56. It should then be noted that under normal advancement of plunger assembly 18 into reservoir 12 for forcing the drug therefrom, spring contact 80 biases lead screw 28 out of its first axial position such that switch member 62 is not actuated since the axial force necessary to advance plunger assembly 18 into reservoir 12 is less than the biasing force of spring contact 80. However, if the axial force necessary to advance plunger assembly 18 into reservoir 12 is increased due to excessive reservoir back pressure caused by an occlusion in the medication tube or delivery apparatus, due to excessive plunger assembly movement friction within reservoir 12, due to a depleted reservoir 12, or due to like conditions, the axial force necessary to advance plunger assembly 18 into reservoir 12 is greater than the biasing force of spring contact 80 such that lead screw 28 moves axially against the bias of spring contact 80 into its first axial position such that first end 44 of lead screw 28 moves contact 80 to electrically engage contact 64 actuating switch member 62 which through the system microprocessor interrupts operation of motor 46 and thus interrupts rotation of lead screw 28. It is then necessary for the operator to cure the reservoir or delivery condition which caused lead screw 28 to move into its first axial position before operation of motor 46 can be resumed.

It should then be noted that prior syringe-type pumps often included approaches for interrupting rotation of the lead screw in the event of excess back pressure in advancing the plunger assembly into the syringe barrel. It can then be further appreciated that drug delivery system 10 according to the teachings of the present invention is then advantageous and patentably distinct from these prior approaches. For example, such prior approaches include multi-component, complicated constructions having clutch mechanisms, stabilizing rods, fingers, and like components which are relatively expensive to manufacture and assemble and which are more prone to wear and break down. Drug delivery system 10 according to the teachings of the present invention is of a simplified construction which utilizes a biased lead screw 28 to itself actuate switch member 62. Thus, drug delivery system 10 according to the teachings of the present invention eliminates the many extra components required in prior approaches and greatly increases the ease of assembly.

Additionally, drug delivery system 10 according to the teachings of the present invention permits the effective water-resistant seal of housing 22 and the components located therein. Specifically, lead screw 28 is the only moving part outside of housing 22 according to the teachings of the present invention and can be easily sealed with low friction commercial shaft seal. Prior approaches often include many parts which were external of the housing which can not be effectively sealed without introducing friction which interferes with operation sensitivity.

Further, it should be noted switch member 62 of drug delivery system 10 according to the teachings of the present invention is particularly advantageous. For example, abutting end 44 of lead screw 28 intermediate spring contact 80 allows a leverage advantage to be obtained. Specifically, the distance between engagement detent 74 and leg 72 can be increased to prevent unintended contact actuation such as from vibration and like external forces while reducing the axial displacement of lead screw 28 required to move contact 80 to electrically engage contact 64. Thus, greater sensitivity of switch member 62 is obtained due to the preferred arrangement of the teachings of the present invention.

Likewise, prior approaches often used microswitches or similar devices which typically require distances of at least 0.020 inches travel to activate and reset. Thus, delivery in prior devices is reduced for a longer time as pressure builds within the syringe resulting in a drug delivery shortfall to the patient. Drug delivery system 10 according to the teachings of the present invention requires only limited axial motion of lead screw 28 to activate and reset switch member 62 reducing drug shortfall during pressure buildup. Further, the drug delivery tube and drug delivery system according to the teachings of the present invention are fabricated in a manner to be less compliant to pressure, i.e. have a lesser tendency to expand under pressure, to further reduce drug delivery shortfall to the patient.

Furthermore, contact 80 of switch member 62 can be preloaded with the desired thrust threshold according to the teachings of the present invention. Thus, no motion of contact 80 will occur until the preloaded thrust threshold is exceeded.

Similarly, adjusting member 84 according to the teachings of the present invention is further advantageous. Specifically, the actuation force on lead screw 28 required to actuate switch member 62 can be individually fixed for each drug delivery system 10. Thus, variability between spring contacts 80 of different biasing forces with normal mass produced tolerances can be eliminated by utilizing member 84.

Now that the basic teachings of the present invention have been explained, many extensions and variations will be obvious to one having ordinary skill in the art. For example, although in the most preferred embodiment according to the teachings of the present invention, lead screw 28 is biased by spring contact 80 and is believed to be advantageous for the reasons set forth hereinbefore and due to the double function of a single component reducing system complexity, lead screw 28 may be biased by other means.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. System for delivering a drug to a patient including a reservoir for storing the drug to be delivered to the patient by the system and a plunger assembly reciprocally received in the reservoir for forcing the drug to the patient from the reservoir when advanced into the reservoir, with the plunger assembly having a free end, comprising, in combination: a chassis; a lead screw having a first end; means for mounting the lead screw for rotation and at least limited axial movement from a first axial position with respect to the chassis; a motor having an output shaft; means for rotatably relating the output shaft of the motor with the lead screw for rotating the lead screw with respect to the chassis; a drive nut threadably received on the lead screw and removeably attached in a nonrotatable manner to the free end of the plunger assembly for advancing the plunger assembly in the reservoir in response to the rotation of the lead screw by the motor and the rotatably relating means; and switch means actuated by the first end of the lead screw for electrically interrupting the operation of the motor when the lead screw is moved into its first axial position as the result of an increase of force necessary to advance the plunger assembly into the reservoir due to excessive reservoir back pressure caused by occlusion, plunger assembly friction, a depleted reservoir, and like conditions, with the switch means including means for axially biasing the lead screw with respect to the chassis out of its first axial position and in the direction of axial movement of the plunger assembly for advancing the plunger assembly into the reservoir for forcing the drug from the reservoir.

2. The drug delivery system of claim 1 wherein the switch means comprises, in combination: a first contact held in a spaced relation from the chassis; and a second contact in a normally spaced condition from the first contact, with the first end of the lead screw abutting with the second contact in its first axial position and moving the second contact to electrically engage the first contact.

3. The drug delivery system of claim 2 wherein the second contact comprises a spring contact for axially biasing the lead screw with respect to the chassis out of its first axial position and in the direction of axial movement of the plunger assembly for advancing the plunger assembly into the reservoir for forcing the drug from the reservoir.

4. The drug delivery system of claim 3 further comprising in combination: means for providing a preset thrust threshold before the second, spring contact electrically engages the first contact.

5. The drug delivery system of claim 4 wherein the preset thrust threshold providing means comprises a spacer located intermediate the second, spring contact and the chassis.

6. The drug delivery system of claim 3 further comprising, in combination: means for adjusting the amount of the increase of force necessary to interrupt the operation of the motor by the switch means.

7. The drug delivery system of claim 6 wherein the adjusting means comprises, in combination: means for adjusting the spacing of the first contact from the chassis.

8. The drug delivery system of claim 7 wherein the spacing adjusting means comprises a set screw threadably received in the chassis and abutting with the first contact for adjusting the spacing between the chassis and the first contact and between the first and second contacts.

9. The drug delivery system of claim 1 wherein the rotatably relating means includes a gear slidably mounted and rotatably fixed to the lead screw; and wherein the drug delivery system further comprises, in combination: a wave-spring washer located between the chassis and the lead screw gear.

10. System for delivering a drug to a patient including a reservoir for storing the drug to be delivered to the patient by the system and a plunger assembly reciprocally received in the reservoir for forcing the drug to the patient from the reservoir when advanced into the reservoir comprising, in combination: a chassis; a lead screw having a first end; means for mounting the lead screw for rotation and at least limited axial movement from a first axial position with respect to the chassis, with the lead screw being axially biased with respect to the chassis out of its first axial position and in the direction of axial movement of the plunger assembly for advancing the plunger assembly into the reservoir for forcing the drug from the reservoir; means for rotating the lead screw with respect to the chassis; means for axially advancing the plunger assembly with respect to the reservoir acting in cooperation with the lead screw and its rotation produced by the rotating means; and means actuated by the first end of the lead screw for interrupting the operation of the rotating means when the lead screw is moved into its first axial position against the bias of the lead screw as the result of an increase of force necessary to advance the plunger assembly into the reservoir due to excessive reservoir back pressure caused by occlusion, plunger assembly friction, a depleted reservoir, and like conditions.

11. The drug delivery system of claim 10 wherein the operation interrupting means comprises, in combination: switch means actuated by the first end of the lead screw for electrically interrupting of the rotating means.

12. The drug delivery system of claim 11 wherein the switch means comprises, in combination: a first contact held in a spaced relation from the chassis; and a second contact in a normally spaced condition from the first contact, with the first end of the lead screw abutting with the second contact in its first axial position and moving the second contact to electrically engage the first contact.

13. The drug delivery system of claim 12 wherein the second contact comprises a spring contact for axially biasing the lead screw with respect to the chassis out of its first axial position and in the direction of axial movement of the plunger assembly for advancing the plunger assembly into the reservoir for forcing the drug from the reservoir.

14. The drug delivery system of claim 13 further comprising, in combination: means for providing a preset thrust threshold before the second contact electrically engages the first contact comprising a spacer located intermediate the second, spring contact and the chassis.

15. The drug delivery system of claim 13 further comprising, in combination: means for adjusting the amount of the increase of force necessary to interrupt the operation of the rotating means by the interrupting means.

16. The drug delivery system of claim 15 wherein the adjusting means comprises, in combination: means for adjusting the spacing of the first contact from the chassis.

17. The drug delivery system of claim 16 wherein the spacing adjusting means comprises a set screw threadably received in the chassis and abutting with the first contact for adjusting the spacing between the chassis and the first contact and between the first and second contacts.

18. The drug delivery system of claim 10 wherein the rotating means includes a gear slideably mounted and rotatably fixed to the lead screw; and wherein the drug delivery system further comprises, in combination: a wave-spring washer located on the lead screw between the chassis and the lead screw gear.

19. The drug delivery system of claim 18 wherein the rotating means comprises, in combination: a motor having an output shaft; and gearing means for rotatably relating the output shaft of the motor with the lead screw gear, with at least limited axial movement being allowed between the lead screw gear and the gearing means.

20. The drug delivery system of claim 10 further comprising, in combination: means for adjusting the amount of the increase of force necessary to interrupt the operation of the rotating means by the interrupting means.

21. In a system for delivering a drug to a patient including a reservoir for storing the drug to be delivered to the patient by the system and a plunger assembly reciprocally received in the reservoir for forcing the drug to the patient from the reservoir when advanced into the reservoir, a chassis, and means for axially advancing the plunger assembly into the reservoir, with the axially advancing means having a first end mounted for at least limited axial movement from a first axial position with respect to the chassis, with the improvement comprising switch means actuated by the first end of the axially advancing means for electrically interrupting the axially advancing means comprising, in combination: a first contact held in a spaced relation from the chassis; and a second, spring contact in a normally spaced condition from the first contact, with the first end of the axially advancing means abutting with the second, spring contact in its first axial position and moving the second, spring contact to electrically engage the first contact, with the second, spring contact axially biasing the axially advancing means with respect to the chassis out of its first axial position and in the direction of axial movement of the plunger assembly for advancing the plunger assembly into the reservoir for forcing the drug from the reservoir, with the switch means electrically interrupting the axially advancing means when the first end is moved into its first axial position against the bias of the second, spring contact as the result of an increase of force necessary to advance the plunger assembly into the reservoir due to excessive reservoir back pressure caused by occlusion, plunger assembly friction, a depleted reservoir, and like conditions.

22. The drug delivery system of claim 21 further comprising, in combination: means for providing a preset thrust threshold before the second, spring contact electrically engages the first contact.

23. The drug delivery system of claim 22 wherein the preset thrust threshold providing means comprises, in combination: a spacer located intermediate the second, spring contact and the chassis.

24. The drug delivery system of claim 21 further comprising, in combination: means for adjusting the amount of the increase of force necessary to electrically interrupt the axially advancing means by the switch means.

25. The drug delivery system of claim 24 wherein the adjusting means comprises, in combination: means for adjusting the spacing of the first contact from the chassis.

26. The drug delivery system of claim 25 wherein the spacing adjusting means comprises a set screw threadably received in the chassis and abutting with the first contact for adjusting the spacing between the chassis and the first contact and between the first contact and the second, spring contact.

27. The drug delivery system of claim 21 wherein the axially advancing means comprises, in combination: a lead screw; means for mounting the lead screw for rotation and at least limited axial movement with respect to the chassis; means for rotating the lead screw with respect to the chassis; and means for axially advancing the plunger assembly with respect to the reservoir acting in cooperation with the lead screw and its rotation produced by the rotating means.

28. The drug delivery system of claim 27 wherein the first end is located ont he lead screw.

29. The drug delivery system of claim 27 wherein the rotating means includes a gear slideably mounted and rotatably fixed to the lead screw; and wherein the drug delivery system further comprises, in combination: a wave-spring washer located on the lead screw between the chassis and the lead screw gear.

30. The drug delivery system of claim 29 wherein the rotating means comprises, in combination: a motor having an output shaft; and gearing means for rotatably relating the output shaft of the motor with the lead screw gear, with at least limited axial movement being allowed between the lead screw gear and the gearing means.

31. The drug delivery system of claim 21 wherein the second, spring contact has a first, secured end secured to the chassis and a second, free end, with the the second, spring contact electrically engaging the first contact adjacent to its second, free end, with the first end of the axially advancing means abutting with the second, spring contact intermediate its first, secured end and its second, free end to allow a leverage advantage to be obtained.

* * * * *

UNITED STATES PATENT OFFICE
CERTIFICATE OF CORRECTION

Patent No. 4,731,058   Dated March 15, 1988

Inventor(s) Phong D. Doan

It is certified that error appears in the above-identified patent and that said Letters Patent are hereby corrected as shown below:

Column 9, line 1, after "interrupting" insert --the control--.

Signed and Sealed this

Sixteenth Day of August, 1988

Attest:

DONALD J. QUIGG

Attesting Officer    Commissioner of Patents and Trademarks